(12) United States Patent
Bianco et al.

(10) Patent No.: US 11,065,110 B2
(45) Date of Patent: Jul. 20, 2021

(54) CALCIFIED ANNULUS MODEL FOR TRANSCATHETER AORTIC VALVE REPLACEMENT

(71) Applicant: Regents of the University of Minnesota, Minneapolis, MN (US)

(72) Inventors: Richard W. Bianco, Minneapolis, MN (US); John P. Carney, Saint Paul, MN (US); Matthew T. Lahti, Woodbury, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/874,669

(22) Filed: Jan. 18, 2018

(65) Prior Publication Data
US 2018/0206981 A1    Jul. 26, 2018

Related U.S. Application Data

(60) Provisional application No. 62/448,089, filed on Jan. 19, 2017.

(51) Int. Cl.
*A61F 2/24* (2006.01)
*A61B 6/12* (2006.01)
*A61B 6/00* (2006.01)
*A61B 17/00* (2006.01)
*A61F 2/00* (2006.01)
*A61L 27/14* (2006.01)

(52) U.S. Cl.
CPC .............. *A61F 2/2409* (2013.01); *A61B 6/12* (2013.01); *A61B 6/487* (2013.01); *A61B 2017/00707* (2013.01); *A61F 2/0077* (2013.01); *A61F 2220/0075* (2013.01); *A61F 2230/0006* (2013.01); *A61F 2230/0013* (2013.01); *A61F 2230/0065* (2013.01); *A61F 2250/006* (2013.01); *A61F 2250/0098* (2013.01); *A61F 2310/00568* (2013.01); *A61L 27/14* (2013.01)

(58) Field of Classification Search
CPC ........................................ A61F 2/2442–2/2448
See application file for complete search history.

(56) References Cited

U.S. PATENT DOCUMENTS

| | | | | |
|---|---|---|---|---|
| 5,716,397 A | * | 2/1998 | Myers | A61F 2/2445 606/1 |
| 2003/0040793 A1 | * | 2/2003 | Marquez | A61F 2/2445 623/2.36 |
| 2006/0020336 A1 | * | 1/2006 | Liddicoat | A61B 17/0644 623/2.37 |
| 2006/0195134 A1 | * | 8/2006 | Crittenden | A61F 2/2445 606/192 |

OTHER PUBLICATIONS

Babaliaros, A., et al., "The Expansion of Transcatheter Technology to Ttreat Aortic Insufficiency: Everthing old becomes new again", JACC Cardiovasc Interv., 7(10):, (2014), 1175-1176.
(Continued)

*Primary Examiner* — Leslie Lopez
(74) *Attorney, Agent, or Firm* — Schwegman Lundberg & Woessner, P.A.

(57) ABSTRACT

A device includes an annular, elastic band having a rectangular cross section. A foil band is affixed to a surface of the elastic band. A contiguous fabric sheath is configured to encase the elastic band and foil band.

20 Claims, 5 Drawing Sheets

(56) References Cited

OTHER PUBLICATIONS

Bajona, P., et al., "Outcomes of Surgical Aortic Valve Replacement: The Benchmark for Percutaneous Therapies", Prog Cardiovasc Dis., 56(6), (2014), 619-624.
Bourantas, C. V., et al., "Evolution of transcatheter aortic valve replacement", Circ Res., 114(6), (2014), 1037-1051.
Cai, J., et al., "Preliminary feasibility and hemodynamic performance of a newly-developed self-expanding bioprosthesis and 16-F delivery system in transcatheter aortic valve mplantation in sheep", J Biomed Res., 26(3), (2012), 211-218.
Cribier, A., et al., "Development of transcatheter aortic valve implantation (TAVI): A heart-warming adventure.", Eur Geriatr Med., 4(6), (2013), 401-406.
Cribier, A., et al., "Development of transcatheter aortic valve implantation (TAVI): A 20-year odyssey", Archives of Cardiovascular Disease, 105(3):, (2012), 146-152.
Dewey, T. M., et al., "Transapical Aortic Valve Implantation?: An Animal Feasibility Study", Ann Thorac Surg., 82(1), (2006), 110-116.
Dvir, D., et al., "Transcatheter Aortic Valve-in-Valve Implantation for Patients With Degenerative Surgical Bioprosthetic Valves", Curr Probl Cardiol., 39(1), (2014), 7-27.
Emmert, M. Y., et al., "Transcatheter aortic valve implantation using anatomically oriented, marrow stromal cell-based, stented, tissue-engineered heart valves: technical onsiderations and implications for translational cell-based heart valve concepts", Eur J Cardio-Thoracic Surg., 45(1), (2014), 61-68.
Horvath, K. A., et al., "Transapical sutureless aortic valve implantation under magnetic resonance imaging guidance: Acute and short-term results", J Thorac Cardiovasc Surg. 149(4), (2015;), 1067-1072.
Leon, M. M., "ranscatheter Aortic Valve Replacement in Patients with Critical Aortic Stenosis: Rationale, Device Descriptions, Early Clinical Experiences, and Perspectives", Semin Thorac Cardiovasc Surg., 18(2), (2006), 165-174.
Mazilu, D., et al., "Self-Expanding Stent and Delivery System for Aortic Valve Replacement", J Med Device, 6(4), (2012), 41006-1-41006-9.
Miller, J. G. et al., "Real-time magnetic resonance imaging-guided transcatheter aortic valve replacement", J Thorac Cardiovasc Surg., 151(5), (2016), 1269-1277.
Miller, J. G., et al., "Robot-assisted real-time magnetic resonance image-guided transcatheter aortic valve replacement", J Thorac Cardiovasc Surg., 151(5), (2016), 1407-1412.
Mozaffarian, D., et al., "Heart Disease and Stroke Statistics—2016 Update", Circulation, 133(4), (2016), e38-e360, e599.
Nakatsuma, K., et al., "Antegrade transcatheter aortic valve implantation using the looped Inoue balloon technique: A pilot study in a swine model", J Cardiol., 69(1), (2017), 260-263.
Paradis, J.-M., et al., "Aortic stenosis and coronary artery disease: What do we know? What don't we know? A comprehensive review of the literature with proposed treatment algorithms", Eur Heart J., 35(31, (2014), 2069-2082.
Rajamannan, N. M., "Calcific Aortic Stenosis: Lessons Learned From Experimental and Clinical Studies", Arterioscler Thromb Vasc Biol., 29(2):, (2009), 162-168.
Schomburg, J. L., et al., "Internal Aortic Annuloplasty: A Novel Technique.", J Investig Surg., 24(5), (2011), 222-226.
Smith, C. R., et al., "Transcatheter Versus Surgical Aortic-Valve Replacement in High-Risk Patients", N Engl J Med., 364(23):, (2011), 2187-2198.
Waksman, R., et al., "Will TAVR Become the Default Treatment for Patients With Severe Aortic Stenosis?", J Am Coll Cardiol., 66(2), (2015), 122-124.
Webb, J. G., et al., "A Randomized Evaluation of the SAPIEN XT Transcatheter Heart Valve System in Patients With Aortic Stenosis Who Are Not Candidates for Surgery", JACC Cardiovasc Interv., 8(14), (2015), 1797-1806.
Webb, J. G., et al., "Transcatheter aortic valve implantation: The evolution of prostheses, delivery systems and approaches", Archives of Cardiovascular Disease, 105(3), (2012), 153-159.
Wendt, D., et al., "A new self-expandable transcatheter aortic valve for transapical implantation: feasibility in acute and chronic animal experiments", Scand Cardiovasc J.;47(3), (2013), 145-153.
Witte, M. B., et al., "General Principles of Wound Healing", Surg Clin North Am., 77(3), (1997), 509-528.
Zeeshan, A., et al., "Transcatheter aortic valve replacement: History and current indications", Cleve Clin J Med., 82(12 Suppl 2), (Dec. 2015), S6-S10.

* cited by examiner

CALCIFIED ANNULUS MODEL FOR TRANSCATHETER AORTIC VALVE REPLACEMENT

CLAIM OF PRIORITY

This patent application claims the benefit of priority of U.S. Provisional Patent Application Ser. No. 62/448,089, filed 19 Jan. 2017, which is hereby incorporated by reference herein in its entirety.

BACKGROUND

Transcatheter aortic valve replacement (TAVR) has emerged as an effective treatment option for patients with symptomatic aortic stenosis (AS) with high surgical risk. A TAVR device is deployed into the aortic annulus. Primary fixation of the device within the annulus is dependent on the resistance of a calcified aortic valve opposing the radial expansion of the TAVR stent.

The absence of a stenotic or calcific aortic annulus presents a challenge in evaluating TAVR devices in large animal models. Leaflet and annular calcification may not be present in the healthy large animal model, and thus, anchoring of clinically applicable TAVR devices is not comparable to what is present in the clinical setting. This presents a challenge for the long-term preclinical evaluation of TAVR devices in a clinically-relevant animal model.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
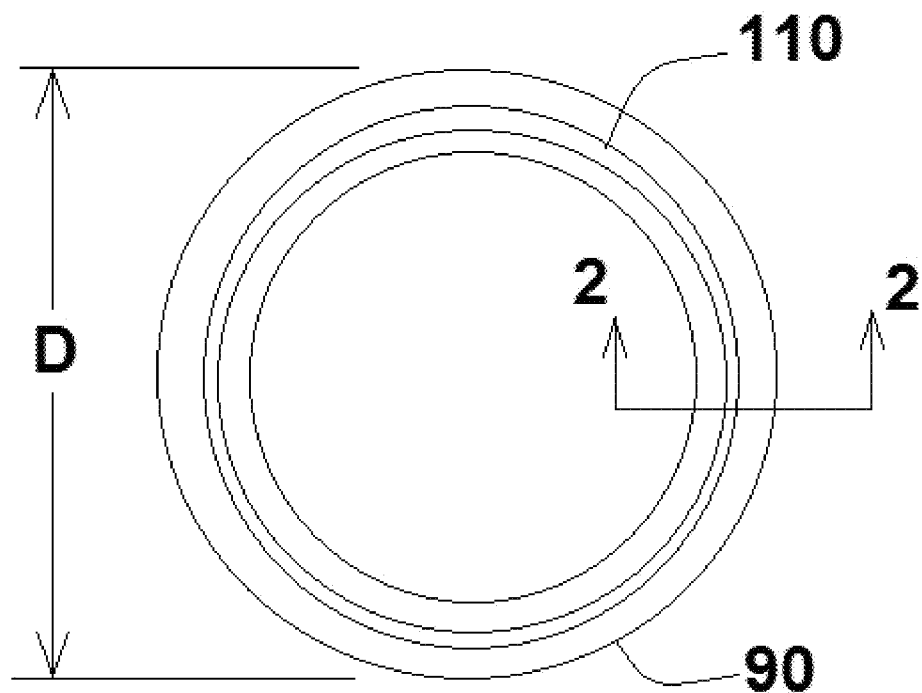
FIG. 1 illustrates a view of a device, according to one example.

Proper placement and anchoring of a transcatheter aortic valve replacement (TAVR) device in humans is dependent on disease. For example, absent a disease condition including annular calcification and aortic stenosis, the placement and anchoring of a TAVR device in a human is frustrated.

Prior to human use, the safety and performance of a new TAVR device must be evaluated in a large animal model. However, healthy animals lack a stenotic aortic annulus, a critical impediment to long-term TAVR device evaluation. Some techniques have been developed to circumvent this problem and secure TAVR devices for chronic use in animal models, including the Hufnagel position, valve-in-valve deployment, and supra-valvular aortic banding. However, these techniques are flawed, difficult to reproduce and challenging for follow up. At this time there is no animal model of aortic stenosis that mimics human pathology, valvular stenosis and calcification at the level of the native aortic annulus.

A TAVR device can be deployed into a healthy aortic annulus of a large animal. Devices deployed in this manner are prone to migration and extreme risk of catastrophic failure. Mortality is well documented in published literature. A TAVR device can be sewn into the native healthy aorta while under cardiopulmonary bypass, however, this approach is often not clinically relevant. A sewn approach is not viable with human patients, as a TAVR device is placed and anchored using minimally invasive procedures.

An example of the present subject matter includes a calcified annulus model that effectively creates and models the disease state conducive for anchoring a TAVR device in a human patient. One example allows for a TAVR device to be deployed in the same manner and in the same position in the large animal model, as it would in a human patient.

An example includes an aortic ring, placed and anchored using a particular surgical technique, and creates a simulated calcific, stenotic, aortic annulus for TAVR implantation in large animal models.

An example of the present subject matter is directed to a simulated calcified annulus model (CAM) for the preclinical assessment of a TAVR device. In one example, an implantable device is configured to simulate a calcified annulus. The device can facilitate training of medical professionals. The device can be used to evaluate devices for efficacy and safety. In one example, the device can facilitate development of improved products.

One example includes a model of aortic stenosis in a large animal model. The model enables long term evaluation of a TAVR device. An example includes a calcified annulus model having a ring structure delivered via a surgical procedure.

One example includes a ring having an outer dimension configured to couple with tissue directly below the aortic valve and having an inner dimension configured for receiving a transcatheter aortic valve replacement device. The aortic stenosis model can be fabricated by implanting a device as described herein. In one example, the device includes a silicone core covered in Dacron fabric. The material can be produced using standard manufacturing procedures and can be sterilized appropriately prior to implant.

The model can be fabricated in a consistent and reproducible manner to accurately model real-world conditions.

A device includes an elastic inner band in the form of an annulus, lined with a foil band and encased in a fabric sheath. This is described as follows.

FIG. 1 illustrates a view of band 90, according to one example. Band 90 is configured as an annular ring. Band 90 can have a circular and planar shape as shown in the figure. Band 90 has a closed, continuous periphery. There are no demarcations indicating transitions in the composition of the ring; the ring is the same throughout the structure. As shown in the figure, foil band 110 is disposed on a surface of band 90.

Figure 2:
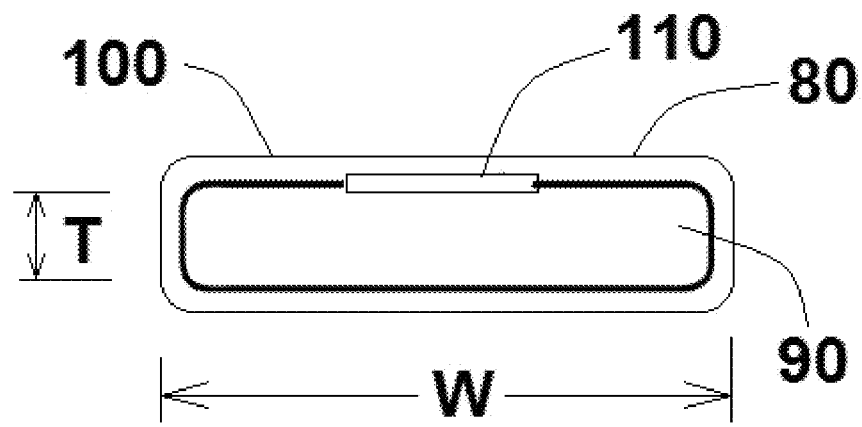
FIG. 2 illustrates a section view of a device, according to one example.

FIG. 2 illustrates a section view of device 100 fabricated using band 90 with the view taken along cut line 2-2, according to one example. In the figure, device 100 includes a circular molded silicone band 90. The width (denoted W) of device 100, in one example, is 5 mm. The thickness (denoted T) of device 100, in one example, is 1 mm. Device 100 forms a continuous circle having a diameter D of 25 mm, according to one example. Device 100 includes foil band 110. Foil band 110, in one example is 1.5 mm in width and is disposed atop the band 90. In one example, foil band 110 is a continuous circle, however discontinues segments are also contemplated.

Device 100 can be fabricated in dimensions different than those specifically indicated. For example, device 100 can have a diameter larger or smaller than 25 mm. In addition, band 90 can be larger or smaller in both width and height. Furthermore, the diameter of the foil band 110 can be larger, smaller, or foil band 110 can be omitted. Foil band 110 can serve as a marker, and in one example, is viewed as a radiopaque marker. Various materials can provide radiopaque properties. In one example, band 110 includes the metal gold, such as gold foil.

Figure 3:
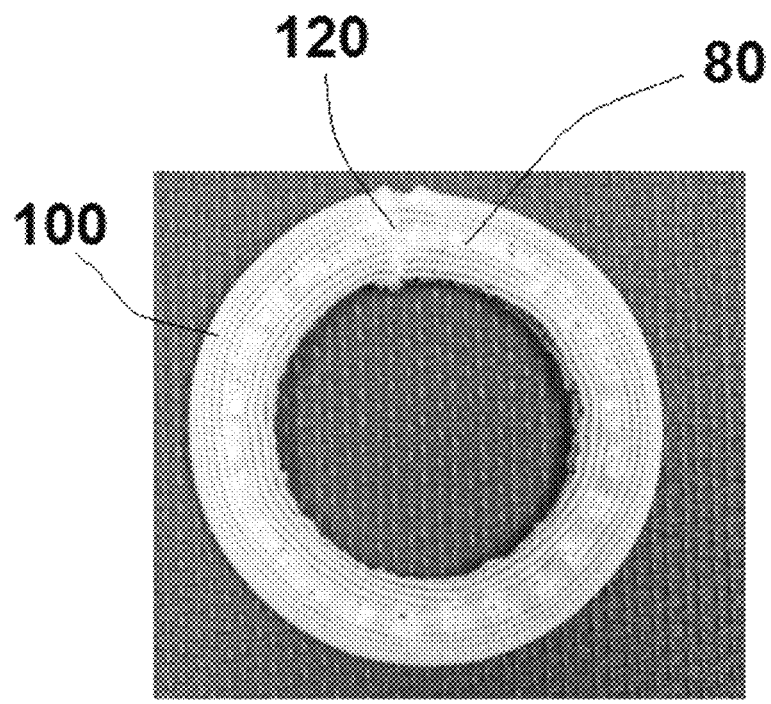
FIG. 3 illustrates a view of a device, according to one example.

FIG. 3 illustrates a view of device 100, according to one example. Device 100 includes fabric sheath 80. In one example, fabric sheath 80 encircles band 90. Fabric sheath 80, in one example, includes a Dacron (polyethylene terephthalate) covering. Fabric sheath 80 is secured to band 90 and foil band 110 with suture 120.

Device 100 is generally flexible. Device 100 can conform to a shape enacted upon it by external force. When force is absent, the device 100 can return to a planar shape.

Figure 4:
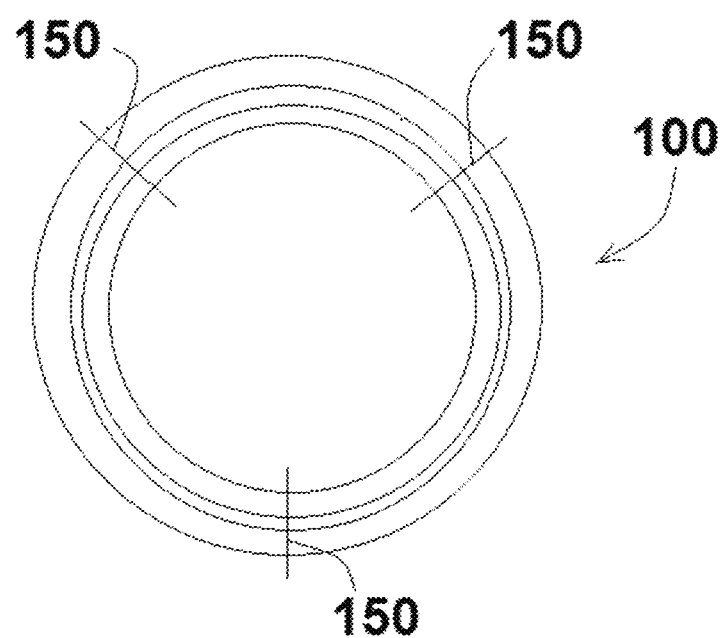
FIG. 4 illustrates a view of a sectioned device, according to one example.

FIG. 4 illustrates device 100 having cut lines 150 indicated. Cut lines 150 segment device 100 into thirds, however, in other examples, the segments are halves, quarters, or other dimension.

Figure 5:
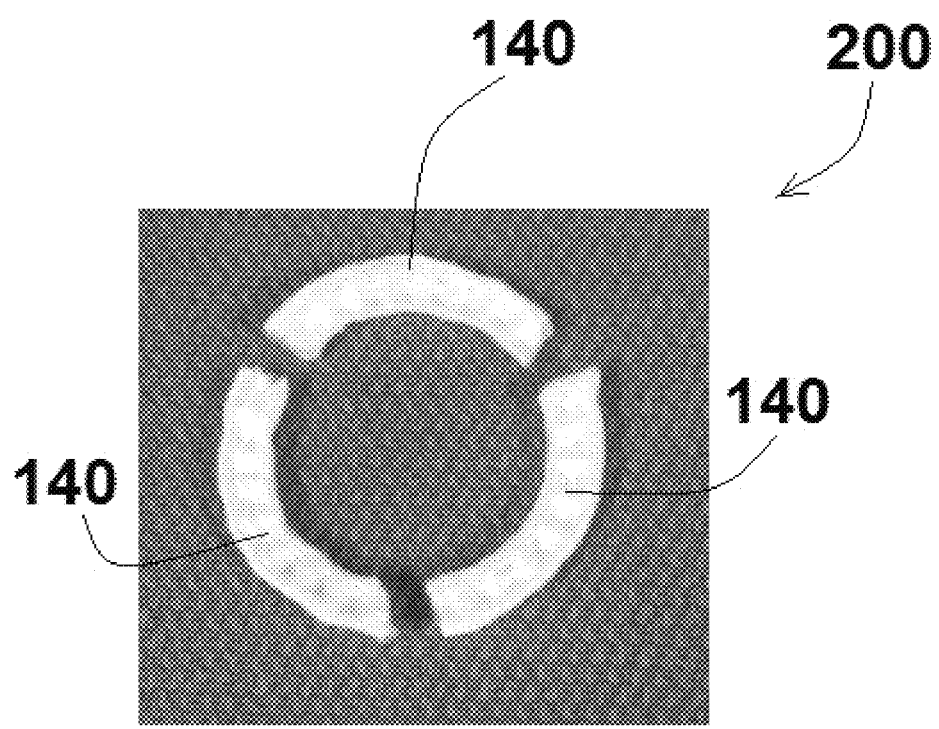
FIG. 5 illustrates a view of a device, according to one example.

FIG. 5 illustrates segmented device 200 derived from device 100, such as that shown in FIG. 4. Device 200 includes a plurality of segments 140, three of which are illustrated in the figure.

Figure 6:
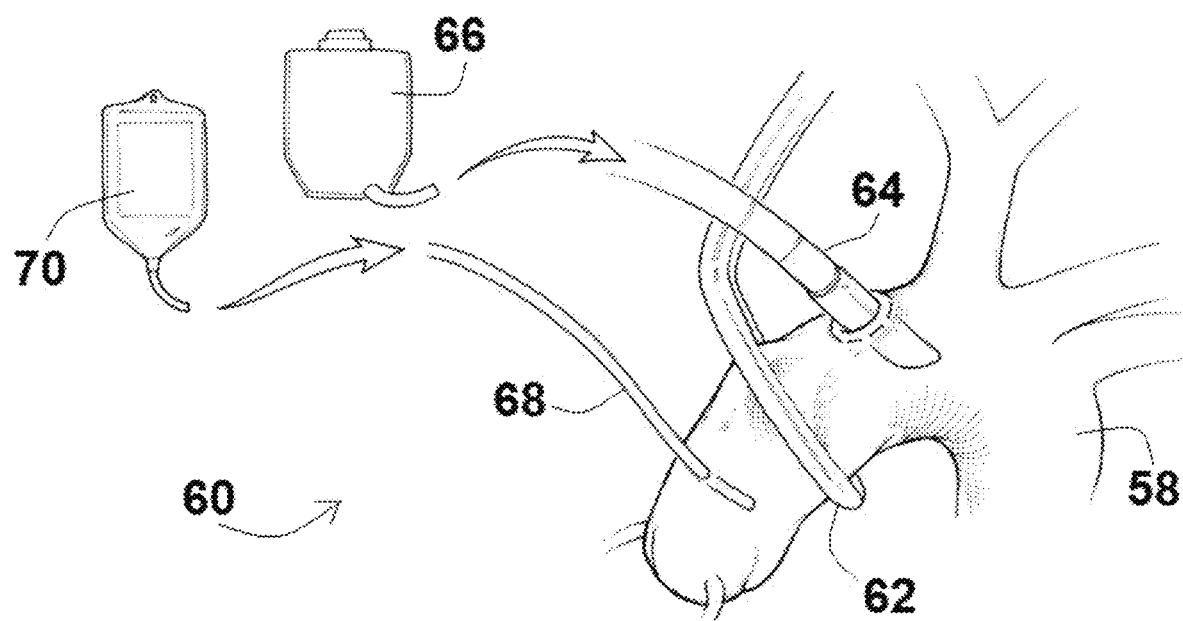
FIG. 6 illustrates treatment of an aorta, according to one example.

FIG. 6 illustrates view 60 showing anatomy 58 in the context of a placement procedure. In the figure, anatomy 58 includes an aorta. Cross clamp 62 is positioned at the aorta. Cannula 64 provide cardiopulmonary bypass from a cardiopulmonary bypass machine. View 60 also depicts cardioplegia solution 70 administered by line 68.

One example includes a particular aortic surgical technique suitable for use with a large animal model. The technique can be described as follows.

One example of the present subject matter includes an aortic surgical procedure that can be performed in large animals and using a ring-shaped, such as device 100. Device 100, either alone or in conjunction with an annuloplasty procedure, can serve as a model of aortic stenosis. One example of the present subject matter can be used for the long term evaluation of a TAVR device in large animal models.

Following aortic surgical procedure in the large animal model, the animal is allowed to heal. During this time, the ring segments, such as section 140, will scar into the native aorta, effectively modeling a stenotic aortic annulus. This allows for delivery and deployment of a TAVR device within the aorta of the large animal, effectively modeling proper TAVR use in a human patient. A radial force of the TAVR stent opposing the healed ring sections, within the aorta, effectively secures the TAVR device within the aorta for long term evaluation of the TAVR device.

Figure 7:
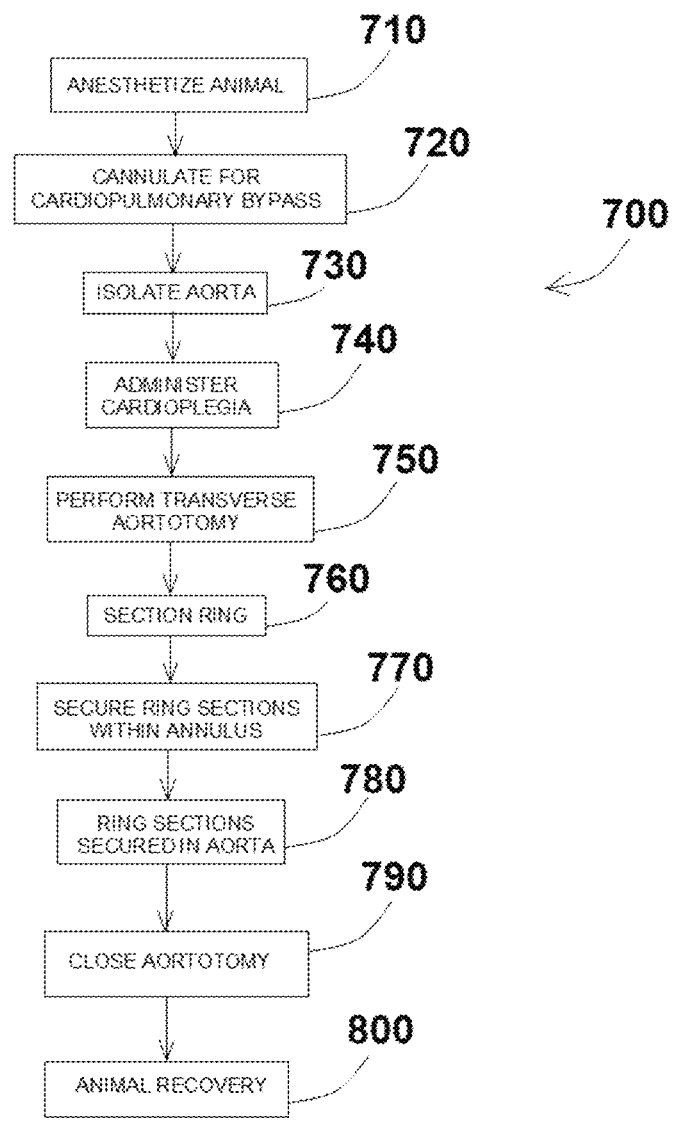
FIG. 7 illustrates a method, according to one example.

FIG. 7 illustrates method 700 according to one example.

At 710, the large animal is anesthetized using conventional techniques well-described in the literature. After transporting the animal to the operating room, the animal can be cannulated, at 720, for cardiopulmonary bypass. After cardiopulmonary bypass is initiated, the aortic procedure can be performed.

At 730, the aorta is carefully isolated from surrounding structures using standard techniques. For example, the aorta is cross clamped proximal to the junction of the brachiocephalic trunk. A cardioplegia catheter is inserted into the aorta proximal to the cross clamp, and at 740, cold cardioplegia is administered through the catheter until cardiac arrest. Cardioplegia is administered into the coronary arteries every 15 minutes throughout the case. A topical saline slush is applied to the heart to maintain a protective temperature and minimize mechanical function.

After removing the cardioplegia catheter, at 750, a transverse aortotomy is performed. After the aortic annulus and leaflets are exposed, the ring is cut into three appropriately sized sections, at 760. Each ring section, such as section 140, is then secured within the annulus, at 770, using one or two interrupted, double armed, braided polyester sutures.

Braided polyester sutures are placed supravalvularly in the aortic sinuses, passing paravalvularly through the wall of the aorta before exiting the aortic wall subvalvularly. Each suture arm is then placed through the ring section. Ring sections are then lowered into the aorta, into the subvalvular region immediately below each native aortic leaflet. Prior to securing the ring sections into the aorta, each section is examined to verify appropriate positioning, as to not impinge native aortic leaflet motion. Sutures are then tied against the ring sections, at 780, using standard surgical knots. After tying knots, suture tails are cut short to the knot to minimize thrombogenecity. After all three ring sections are secured, the aortotomy is closed, at 790, with polypropylene suture, using standard techniques.

In one example, the ring sections are positioned under the aortic valve at a location in the left ventricle.

At 800, the large animal is weaned from cardiopulmonary bypass using standard techniques. Operative incisions are closed, and the animal weaned from mechanical ventilation using conventional techniques. The animal is allowed time to recover and heal for a period approximately 30 postoperative days or greater.

Simulated Calcified Annulus Model—Method of Use

Approximately thirty days after the implantation procedure, the segments will be covered in a fibrous pannus sheath, appearing scarred and thickened. The ring segments will protrude within the native aortic annulus, simulating calcific aggregations present in calcific aortic stenosis.

The ring segments will be easily identified via echocardiography, including transthoracic (TTE) transesophageal (TEE) and intracardiac (ICE). Ring segments can be easily identified via x-ray fluoroscopy and with the aid of foil band 110.

Both techniques may be used to identify cardiac structures and aid in the deployment of TAVR devices within the simulated calcified annulus model.

Various Notes

The following describes an example of a Surgical Procedure. The subject animal (large) can be premedicated with sustained release (SR) buprenorphine 0.27 mg/kg SQ within 24 hours prior to surgery. Anesthesia can be induced by administering 0.04 mg/kg atropine IM, 10 mg/kg Ketamine (IM) and 2-6 mg/kg propofol (IV). The animal can then be intubated, maintained on isoflurane at 2-4% for the duration of surgery and monitored for heart rate, mean blood pressure, fixed pupil location, corneal reflex absence, and oxygen saturation to ensure proper anesthesia.

Surgery can be performed in the right decubitus position with left 3rd intercostal space thoracotomy to expose the heart and the aorta. The animal can be anticoagulated with 250 IU/kg heparin IV and given 125 mg methylprednisolone IV. The can be initiated on cardiopulmonary bypass through a standard approach, with the aortic cannula in the descending aorta and directed cranially as well as an appropriately sized, multi staged, venous return cannula placed in the right atrial appendage. The animal can be cooled to 28° C., and the aorta cross clamped proximal to the junction of the brachiocephalic trunk.

Partial transverse aortotomy can be made. The aortic annulus can be measured with a sizer, and recorded. An example device can be implanted directly below the native aortic valve leaflets in 3 separate pieces using interrupted 3-0 braided polyester inverted mattress stitches. Aortotomy can be closed, animal rewarmed and decannulated from cardiopulmonary bypass (CPB).

Postoperatively, the animal can recover under the care of a veterinarian and receive keprofen 1-2 mg/kg IM or carprofen 2-4 mg/kg IM as needed for pain management.

TAVR Deployment

An animal can be implanted with a TAVR device. This can be done as a separate procedure 60 days after the creation of the aortic stenosis model. Under general anesthesia, right neck incision can be made and the carotid artery can be exposed and cannulated using the Seldinger technique. The deployment sheath and mechanism can be introduced via the carotid artery. TAVR device can be deployed in the stenotic annulus under fluoroscopy and intracardiac echocardiography (ICE) visualization. The carotid artery can be closed and the animal recovered for 140 days until, for example, scheduled sacrifice.

Endpoint Measurements

All animals can receive follow up with transthoracic echocardiography (TTE) at 14 days and 60 days after the procedure as well as 140 days after TAVR device deployment. Maximum pressure gradient, mean pressure gradient, cardiac output, heart rate and effective orifice area can be collected through TTE. The presence of aortic insufficiency and paravalvular leak, having the TAVR deployed, can be evaluated.

The animal can be euthanized with beuthanasia given intravenously at 87 mg/kg. After death, the animal can undergo heart retrieval for evaluation and device retrieval. Pathological examination can focus on the position of the device in relation to left ventricle and aortic valve leaflets, incorporation into the surrounding tissues and fibrotic scar formation around the material to create a rigid annulus. An animal can undergo extensive necropsy, with examination of the external surface of the animal carcass, all its orifices, and the cervical, thoracic and abdominal regions, cavities and contents.

Follow-up after the implantation procedure and a 60-day study period can show that cardiac echocardiogram (TTE) indicates no functional aortic stenosis, mean pressure gradient of 10.2±4.2 cm H2O at 14 days and 7.0±3.7 cm H2O at 60 days, p value 0.04 (Table 2). The procedure can yield no change in cardiac output, decrease in the heart rate and an increase in effective orifice area over the study period. Mild to moderate aortic insufficiency (AI) may be found in some subject animals after the procedure. Following animal sacrifice after 60 days, the implanted ring segments can form hard, fibrous protrusions into the left ventricle outflow tract.

A subject animal can undergo deployment of a TAVR device. A fluoroscopic view of the implant site and aortic annulus before TAVR deployment can indicate the presence of aortic insufficiency as contrast leaks back into the left ventricle. A TAVR device can be positioned within the aortic annulus formed by the device. Fluoroscopy can show a lack of aortic insufficiency after deployment. TTE pre-deployment and at 140 days after TAVR device can show similar, non-statistically significant hemodynamic parameters: such as mean pressure gradient of 4.6±1.2 cm H2O and 6.5±4.9 cm H2O, respectively, and cardiac output of 8.7±0.13 L/min and 9.1±1.3 L/min, respectively. Heart rate may be elevated at 140 days post operatively, which is statistically significant; however the heart rates can be expected to be within normal range for sheep and likely represented sniffing or anxiety. Typical results can indicate no AI or paravalvular leak present on TTE after TAVR device deployment. Pathology examination of the TAVR animals can show a well healed stenotic aortic annulus, and a well-positioned and tightly anchored TAVR device within the aortic annulus.

Aortic stenosis is calcification and narrowing of the aortic annulus. It is the resistance of the stiff calcified annulus against the radial expansion force of the stent that fixes and anchors the TAVR device in place. An external surface of the TAVR device engages with an internal surface of the formed annulus. A challenge associated with animal models for TAVR device testing has been the anatomically normal, non-calcified aortic annulus. The normal annulus is elastic under the radial expansion force of the stent, thus preventing adequate anchoring of the TAVR device and being subject to device migration and peri-valvular leak. Some techniques have been developed to circumvent this problem, such as deployment of the TAVR valve into the pulmonary valve position, the Hufnagel position (deployment into the descending aorta) or the ascending aorta with banding deployment site. There have also been attempts to deploy over-sized valves into the orthotopic position of the normal aortic valve to overcome the lack of stiff anchoring points of the calcifications with increased radial expansion force. However, even this approach is subject to valve migration as well as peri-valvular leak and aortic insufficiency.

An example of the present subject matter provides a model of aortic stenosis at the native aortic annulus by implanting a device into the annulus. Over time, the prosthetic material is incorporated into the annulus to create a stiff, fibrotic scar. This provides a stiff landing and anchoring platform for TAVR device deployment, similar to how aortic valve calcifications anchor the valves in human patients.

Results indicate good incorporation of the material into the surrounding tissue with formation of a fibrotic scar at the aortic annulus, forming a firm anchoring platform for the TAVR devices. Adequate scar formation can occur at 4-6 weeks after implantation.

Follow up echocardiography data shows that the procedure does not create a functional aortic stenosis or left ventricular outflow obstruction. The maximum and mean pressure gradients across the aortic valve can be expected to be similar at 14 day and 60 days post-operatively, estimated point of satisfactory material incorporation and fibrotic scar formation. Cardiac output and HR can be similar at both time points. Mild to moderate aortic insufficiency may be noted post operatively in some animals. This suggests that the implanted material either alters the shape of the aortic annulus or in some way interferes with the valve leaflets themselves; however this does not appear to translate into negative impact on the hemodynamics, nor is this clinically significant for the animal.

A TAVR device can be deployed into the aortic stenosis model. The animals can thrive clinically, exhibit good hemodynamics on TTE and be free of evidence of AI. Device migration is non-existent or negligible and free of other complications secondary to the model or device deployment.

The implantation procedure is a surgical procedure. During the material implantation there may be a risk of damaging or trapping the native aortic valve leaflets, which leads to severe aortic insufficiency, acute heart failure and inability to wean off of CPB. There is also a risk of damaging the atrioventricular (AV) node or mitral valve leaflets when placing the anchoring sutures, which, again, results in acute heart failure and inability to wean off of CPB. Careful placement of each anchoring suture can avoid the above complications. The amount of implanted material can be adjusted for each annulus based on shape, size and degree of visualization. In one example, adjustment includes cutting the segment to a selected length.

An advantage of the present subject matter is that the model animals can be created in large numbers ahead of time. Allowing for the 4-6 weeks of healing and adequate scar formation at the aortic annulus, the present subject matter allows for rapidly deployment and testing of a large number of TAVR devices at a time. This is in contrast to the ascending aortic band approach, which requires a thoracotomy at the time of the device deployment, significantly reducing the number of devices that can be tested at a given time. The present subject matter can facilitate development of medical devices in a clinically relevant setting.

Another advantage of the present subject matter is the ease of follow up. Because the TAVR devices are deployed in the orthotopic aortic valve position, follow up can be easily accomplished with transthoracic echocardiography (TTE). Ascending aortic band or the descending aorta (Hufnagel) positions are challenging, if not impossible, to visualize/achieve adequate windows for accurate measurements via TTE, since the TAVR device is deeper in the mediastinum or behind the left lung lobe. Alternative follow up modalities such as angiography, transesophageal echocardiography or intra-cardiac echo (ICE) can be used to visualize the above device positions; however, all of those modalities require animal sedation as well as an invasive procedure, which necessitates added expertise and cost to the testing process.

An example of the present subject matter creates stenotic segments in the aortic annulus with adequate rigidity for deployment, anchorage and long-term evaluation of a TAVR device. This procedure provides an animal model that mimics human AS and provides a stable TAVR deployment platform.

In some examples, a segment includes a metal band (such as a foil) or a metal wire. The metal element, such as aluminum, stainless steel, gold, or other base metal, is radiopaque and can aid in placement of the device. A radiopaque material attenuates x-ray radiation and provides light area in an x-ray image. Other materials, or structures, or imaging modalities can also be used to facilitate placement.

The plurality of segments can include any number of segments. In one example, three segments are provided. The three segments can be aligned with the three leaflets of the aortic valve. The segments can be cut to size to fit the animal model.

In one example the present subject matter includes a continuous segment that encircles the inner wall of the tract. In one example, independent segments are arranged end-to-end. Segments are separated by a small gap to allow tissue to stretch with movement. The segments are individually affixed to the wall with sutures.

An elastic core facilitates insertion of the attachment sutures, allows for cinching of the segments into place, and provides good height to promote fibrous tissue growth and promotes healing.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the The claimed invention is:

1. An implantable device for promoting aortic stenosis, the device comprising a plurality of independent segments, each segment including an elastic core encased in a fabric sheath, wherein the plurality of segments are configured for individual placement within a tract and configured to form an annulus in the tract, and wherein each segment is configured for suturing to a wall of the tract and wherein the plurality of segments are configured to engage with an external surface of an aortic valve replacement device, and wherein the plurality of segments are configured as a continuous ring that encircles the tract and wherein the continuous ring is configured for placement at an annulus of a healthy animal in order to create a stenotic state via a calcified annulus into which the aortic valve replacement device can be placed to correct disease created by the stenotic state.

2. The device of claim 1 wherein the plurality of segments includes three segments.

3. The device of claim 1 wherein at least one segment of the plurality of segments includes a radiopaque material coupled to the core or coupled to the sheath.

4. The device of claim 3 wherein the radiopaque material includes a metal.

5. The device of claim 3 wherein the radiopaque material includes a wire or includes a foil.

6. The device of claim 1 wherein the core includes silicone.

7. The device of claim 1 wherein the sheath includes a polymer.

8. The device of claim 1 wherein the sheath includes polyethylene terephthalate.

9. A method of promoting formation of aortic stenosis, the method comprising:
    positioning a plurality of independent segments individually within a tract, each segment having an elastic core encased in a fabric sheath; and
    affixing the plurality of segments to a wall of the tract via sutures, the segments arranged to form a continuous ring that encircles an annulus in the tract, and wherein the plurality of segments are configured to engage with an external surface of an aortic valve replacement device and wherein the continuous ring is configured for placement at the annulus of a healthy animal in order to create a stenotic state via a calcified annulus into which the aortic valve replacement device can be placed to correct disease created by the stenotic state.

10. The method of claim 9 wherein positioning the plurality of segments includes positioning three segments.

11. The method of claim 9 wherein each segment of the plurality of segments is aligned with a leaflet of an aortic valve in the tract.

12. The method of claim 9 wherein affixing the sutures includes passing through the wall and a segment of the plurality of segments.

13. The method of claim 9 wherein positioning the plurality of segments includes fluoroscopically viewing.

14. The method of claim 9 wherein positioning the plurality of segments includes selecting an elongate length for a segment of the plurality of segments.

15. The method of claim 9 wherein positioning the plurality of segments includes positioning "positioning the segments" in end to end relation.

16. A device comprising:
    an elastic band having a rectangular cross section, wherein the elastic band includes a plurality of independent segments, each segment configured for individual end-to-end placement and the elastic band configured as a continuous annular ring;
    a foil band affixed to a surface of each segment of the elastic band; and
    a contiguous fabric sheath encasing each segment of the elastic band and the foil band and wherein the continuous annular ring is configured for placement at an annulus of a healthy animal in order to create a stenotic state via a calcified annulus into which an aortic valve replacement device can be placed to correct disease created by the stenotic state.

17. The device of claim 16 wherein the elastic band includes silicone.

18. The device of claim 16 wherein the foil band includes gold.

19. The device of claim 16 wherein the fabric sheath includes polyethylene terephthalate.

20. The device of claim 16 wherein the fabric sheath includes a sutured joint.

* * * * *